(12) United States Patent
Berge

(10) Patent No.: US 11,061,256 B2
(45) Date of Patent: Jul. 13, 2021

(54) OPHTHALMIC LENS WITH DYNAMIC FOCUS CONTROL

(71) Applicant: LACLAREE, Lyons (FR)

(72) Inventor: Bruno Berge, Lyons (FR)

(73) Assignee: LACLAREE, Lyons (FR)

( * ) Notice: Subject to any disclaimer, the term of this patent is extended or adjusted under 35 U.S.C. 154(b) by 98 days.

(21) Appl. No.: 16/315,780

(22) PCT Filed: Jul. 5, 2017

(86) PCT No.: PCT/EP2017/066722
§ 371 (c)(1),
(2) Date: Jan. 7, 2019

(87) PCT Pub. No.: WO2018/007425
PCT Pub. Date: Jan. 11, 2018

(65) Prior Publication Data
US 2019/0227346 A1    Jul. 25, 2019

(30) Foreign Application Priority Data
Jul. 8, 2016  (FR) ...................................... 16/56610

(51) Int. Cl.
*G02C 7/08*   (2006.01)
*G02C 7/06*   (2006.01)
*G02B 3/14*   (2006.01)
*A61F 2/16*   (2006.01)
*G02B 26/00*  (2006.01)

(52) U.S. Cl.
CPC .............. *G02C 7/085* (2013.01); *G02B 3/14* (2013.01); *G02C 7/06* (2013.01); *A61F 2/1616* (2013.01); *G02B 26/004* (2013.01); *G02C 7/088* (2013.01)

(58) Field of Classification Search
CPC ... G02B 3/14; G02B 3/12; G02B 1/06; G02B 1/041; G02B 3/06; G02B 26/004; G02C 7/085; G02C 7/083; G02C 7/08; G02C 7/06; G02C 7/088; A61B 3/0285; A61B 3/036; A61B 3/04; A61B 3/028; A61B 3/08; A61F 2/1616
USPC ................ 359/665–667, 694, 819, 822, 886; 351/159.01, 159.34, 159.68, 159.73
See application file for complete search history.

(56) References Cited

U.S. PATENT DOCUMENTS 7,675,686 B2   3/2010   Lo et al.
7,773,306 B2   8/2010   Van As et al.
(Continued)

FOREIGN PATENT DOCUMENTS

CN   1784628 A    6/2006
CN   101069106    11/2007
(Continued)

OTHER PUBLICATIONS

English translation of JP H01302301, machine translated on May 11, 2020.*
(Continued)

*Primary Examiner* — Jie Lei
(74) *Attorney, Agent, or Firm* — Cantor Colburn LLP

(57) ABSTRACT

This invention relates to ophthalmic lens for spectacle comprising a primary glass, a secondary glass, a main chamber and a membrane configured to separate the volume of the main chamber in a first chamber and a second chamber.

19 Claims, 2 Drawing Sheets

(56) References Cited

U.S. PATENT DOCUMENTS

| | | | |
|---|---|---|---|
| 8,699,141 B2* | 4/2014 | Aschwanden | H04N 5/2328 359/666 |
| 2003/0095336 A1 | 5/2003 | Floyd | |
| 2007/0211207 A1* | 9/2007 | Lo | G02C 7/085 351/41 |
| 2009/0213471 A1* | 8/2009 | Silver | G02B 26/004 359/665 |
| 2011/0235186 A1 | 9/2011 | Blum et al. | |
| 2011/0261466 A1 | 10/2011 | Buch et al. | |

FOREIGN PATENT DOCUMENTS

| | | |
|---|---|---|
| DE | 102007004080 A1 | 8/2008 |
| JP | 1302301 | 12/1989 |
| JP | 2004233945 A | 8/2004 |
| WO | 2006011937 A2 | 2/2006 |
| WO | 2007049058 A2 | 5/2007 |
| WO | 2012055049 A1 | 5/2012 |
| WO | 2012064955 A2 | 5/2012 |

OTHER PUBLICATIONS

International Search Report for Application No. PCT/EP2017/0066722.
Written Opinion for Application No. PCT/EP2017/0066722.
CN First Office Action for Application No. 201780042593X.
CN Search Report for Application No. 201780042593X.
CN Second Office Action for Application No. 201780042593X.
Translation of CN First Office Action for Application No. 201780042593X.
Translation of CN Second Office Action for Application No. 201780042593X.

* cited by examiner

OPHTHALMIC LENS WITH DYNAMIC FOCUS CONTROL

CROSS REFERENCE TO RELATED APPLICATIONS

This application is a National Stage of PCT Application No. PCT/EP2017/066722 filed on Jul. 5, 2017, which claims priority to French Patent Application No. 16/56610 filed on Jul. 8, 2016 the contents each of which are incorporated herein by reference thereto.

TECHNICAL FIELD OF THE INVENTION

This invention relates to electronic spectacles for patients having trouble with eye-accommodation (presbyopia, accommodation spasm, patients after cataract surgery etc. . . . ). More specifically, this invention relates to ophthalmic lens or lenses.

STATE OF THE ART

Today several solutions exist to compensate for the lack of accommodation of presbyopia patients like spectacles, contact lenses or intraocular lenses for examples.

The patients can wear several pair of spectacles (optimized for near and far vision respectively). However, the use of several pair of spectacles poses problems of ergonomic. Alternatively, Bi-focal spectacles may be used. Bi-focal glasses have an insert in their lower part, which provides near vision when the user looks down. Bi-focal spectacles are essentially reading glasses, the intermediate vision being of poor quality. Progressive lenses have a continuum of corrections from the lower part (reading) to the upper part, they allow some intermediate vision. However, the intermediate vision is sharp only inside a narrow zone, so-called "corridor" of vision, the outside being blurred. Also progressive lenses deform the images considerably, curving straight lines. It is admitted that progressive lenses bring a good image quality when the optical power difference between top and bottom is below 1 diopter. Considering that 3 diopters are needed for a perfect vision between far and near vision for people with fully developed presbyopia, progressive lenses still suffer from lack of image quality.

For contact lenses or intraocular lenses, the main treatment called "monovision" consists in adjusting the contact lenses at two different distances for the left and right eye. This is obviously a compromise which can be uncomfortable, but a user may wear compensating spectacles for a given fixed object distance (reading, intermediate or far). The other option relies on so-called multifocal optics: several images corresponding to far and near distances are projected on the retina. The multifocal solution allows reading and seeing at close and far distances, but always with a somewhat degraded image quality. With this solution, blurred images may be problematic, for instance while driving at night.

Another solution, which can be contemplated, is Lasik or laser Surgery. Unfortunately, presbyopia patients suffer from the same drawbacks than described above: only two possibilities are offered, either monovision, or multifocals. Both solutions may bring discomfort and drawbacks. In addition, surgery is non-reversible.

This invention relates to a solution to the previous problems: glasses with an adjustable optical power. The goal of the solution is to provide a pair of spectacles with glasses which optical power is variable at least in a central portion, the range of variation being up to 3 Diopters. The wearer would benefit from a good vision either at close, intermediate, far or any other distances, by the continuous variation of its glass (or lens) optical power. The spectacle focusing power would be either manually driven, or automatically focusing.

SUMMARY OF THE INVENTION

In order to achieve this objective, the present invention provides, according to a first aspect, an ophthalmic lens for spectacle comprising:
  a primary glass: the primary glass comprises a first transparent material; the primary glass has a first primary surface and a second primary surface, the primary glass is configured to transmit light from the first primary surface to the second primary surface through the first transparent material;
  a secondary glass: the secondary glass comprises a second transparent material; the secondary glass has a first secondary surface and a second secondary surface, the secondary glass is configured to transmit light from the first secondary surface to the second secondary surface through the second transparent material;
  a main chamber: the main chamber has a main volume comprised between the second primary surface and the first secondary surface; and
  a membrane: the membrane comprises a deformable portion, the deformable portion, partially comprised in the main chamber totally separates the main chamber in at least a first chamber configured to comprise at least a primary fluid and a second chamber configured to comprise at least a secondary fluid, the first chamber is comprised between the second primary surface and the deformable portion, the second chamber is comprised between the deformable portion and the first secondary surface,
  characterized in that
  the primary fluid has a first relative density and the secondary fluid has a second relative density; the ratio between the first relative density and the second relative density is comprised between 0.9 and 1.1, in particular between 0.95 and 1.05 and preferably between 0.99 and 1.01.

Such a ratio between the first relative density and the second relative density avoids having a distortion of the membrane due to gravity.

The spectacles with those glasses have an optical power, which is variable at least in a central portion, the range of variation being up to 3 diopters. The wearer would benefit from a good vision either at close, intermediate, far or any other distances, by the continuous deformation of the membrane. In addition, these ophthalmic lenses offer a real sight comfort to the patient.

According to an embodiment of the present invention, the primary glass having a primary glass refractive index and the primary fluid having a primary fluid refractive index are selected to have a difference between the primary glass refractive index and the primary fluid refractive index being comprised between $0.1 \times 10^{-3}$ and $25 \times 10^{-3}$, and/or the secondary glass having a secondary glass refractive index and the secondary fluid having a secondary fluid refractive index are selected to have a difference between the secondary glass refractive index and the secondary fluid refractive index being comprised between $0.1 \times 10^{-3}$ and $25 \times 10^{-3}$.

According to an embodiment of the present invention, the index of refraction is measured at 589 nm.

According to an embodiment of the present invention, the primary glass comprises an intermediate primary surface surrounding at least partially a primary opening, the secondary glass comprises an intermediate secondary surface surrounding at least partially a secondary opening, the intermediate primary surface and the intermediate secondary surface are configured to minimize residual light scattering at their interface.

According to an embodiment of the present invention, the roughness of the intermediate primary and secondary surface is smaller than 100 nm RMS, precisely smaller than 50 nm RMS and preferably smaller than 20 nm RMS.

The RMS roughness, RMS stand for Root Means Square, described in this present application may be measured via a profilometer.

Also, one skilled in the art would design the surface such as the shape of the interface would satisfy a given accuracy level (e.g. a given accuracy level may be lower than $$\frac{\lambda_{Na}}{4},$$

$\lambda_{Na}$ being the Wavelength of a Sodium light).

Thus, this arrangement allows the interface to be as invisible as possible and as effective as possible for correcting refraction errors of the patients at a given object distance.

According to another embodiment of the present invention, the membrane is partially comprised between the intermediate primary surface and the intermediate secondary surface.

Thus, this arrangement allows the membrane to be at the level of the intermediate primary surface and the intermediate secondary surface According to another embodiment of the present invention, the membrane comprises a supporting portion partially comprised between the intermediate primary surface and the intermediate secondary surface, and the supporting portion surrounds the deformable portion.

Thus, this arrangement allows increasing the size of the chambers and simultaneously to decrease the weight or the quantity needed for the primary glass and/or the secondary glass.

According to another embodiment of the present invention, the ophthalmic lens comprises a primary fluid passage comprising a primary channel configured to convey the primary fluid and to emerge into the first chamber; and a secondary fluid passage comprising a secondary channel configured to convey the secondary fluid and to emerge into the second chamber.

Thus, this arrangement allows conveying the primary fluid and the secondary fluid and to emerge into the first chamber and second chamber respectively.

According to another embodiment of the present invention, the primary channel is partially delimited by the primary glass and partially delimited by the membrane or the secondary glass and/or the secondary channel is partially delimited by the secondary glass and partially delimited by the membrane or the primary glass.

Thus, this arrangement allows having a channel in a glass although the pieces are thin and fragile, or for some manufacturing's reasons.

According to another embodiment of the present invention, the primary channel is totally delimited by the primary glass, and/or the secondary channel is totally delimited by the secondary glass.

Thus, this arrangement allows having a channel although the glass is fragile and/or the channel may not be bored.

According to another embodiment of the present invention, the deformable portion is configured to be deformed between a first position, a second position and a rest position located at the level of the primary or secondary opening; the first position and the second position are configured to be located on both sides of the rest position.

Thus, this arrangement allows saving energy when the fluids push the membrane from one position among the first position and the second position, and the rest position. A part of this energy is provided by the elastically deformable property of the deformable portion.

According to another embodiment of the present invention, the first chamber has a first chamber shape and the second chamber has a second chamber shape, the first chamber shape is different of the second chamber shape.

This arrangement avoids superposing the border of the first chamber and the border of the second chamber to reduce the residual visibility of said borders. It may also be easier to manufacture chambers with different shapes depending on the chosen material.

According to another embodiment of the present invention, the membrane thickness is less than 10 µm, in particular the membrane thickness is less than 5 µm and preferably the membrane thickness is less than 1 µm.

According to another embodiment of the present invention, the ratio between the first relative density and the second relative density is comprised between 0.9 and 1.1 and the membrane thickness is less than 10 µm, in particular the ratio between the first relative density and the second relative density is comprised between 0.95 and 1.05 and the membrane thickness is less than 5 µm, and preferably the ratio between the first relative density and the second relative density is comprised between 0.99 and 1.01 and the membrane thickness is less than 1 µm.

The fact that the ratio between the first relative density and the second relative density is around 1 and that the membrane thickness is less than 10 µm allows reducing the stress applied to the membrane, and thus reducing the distortion of the latter.

According to an embodiment of the present invention, the gradient of optical power between top and bottom of the ophthalmic lens is less than 0.25 D. Such a configuration of the ophthalmic lens allows having an improved optical quality.

According to another embodiment of the present invention, the primary glass comprises a first primary glass and a second primary glass, and/or the secondary glass comprises a first secondary glass and a second secondary glass; the first primary glass and a second primary glass have a first primary glass refractive index and the second primary glass refractive index respectively and the first secondary glass and the second secondary glass have a first secondary glass refractive index and the second secondary glass refractive index respectively; the difference between at least one of the first primary glass refractive index and the second primary glass refractive index and the primary fluid refractive index is comprised between $0.1 \times 10^{-3}$ and $25 \times 10^{-3}$ and the difference between at least one of the first secondary glass refractive index and the second secondary glass refractive index and the secondary fluid refractive index being comprised between $0.1 \times 10^{-3}$ and $25 \times 10^{-3}$.

Thus, this arrangement allows the interface between the glass and the fluid to be more or less invisible.

According to another embodiment of the present invention, the primary glass refractive index is greater than the secondary glass refractive index, and/or the first primary glass refractive index is greater than the second secondary glass refractive index.

According to another embodiment of the present invention, the primary glass is configured to transmit light from the first primary surface to the viewer by going through the first secondary surface of the secondary glass.

Thus, this arrangement allows concentrating the lights rays to the patient at far distances with the membrane deformed in one direction, while the membrane being deformed in the other direction for near-vision, thus minimizing the maximum deformation of the membrane, and thus saving energy.

According to another embodiment of the present invention, the second primary glass comprises the primary channel configured to convey the primary fluid and to emerge into the first chamber.

Thus, this arrangement allows the primary fluid to be conveyed.

According to another embodiment of the present invention, the first secondary glass comprises a secondary channel configured to convey the secondary fluid and to emerge into the second chamber.

Thus, this arrangement allows the secondary fluid to be conveyed.

The present invention relates to a spectacle comprising at least one ophthalmic lens according to one of the previous embodiments.

BRIEF DESCRIPTION OF THE DRAWINGS

The foregoing and other purposes, features, aspects and advantages of the invention will become apparent from the following detailed description of embodiments, given by way of illustration and not limitation with reference to the accompanying drawings, in which.

DESCRIPTION OF THE INVENTION

General Principle

Figure 1:
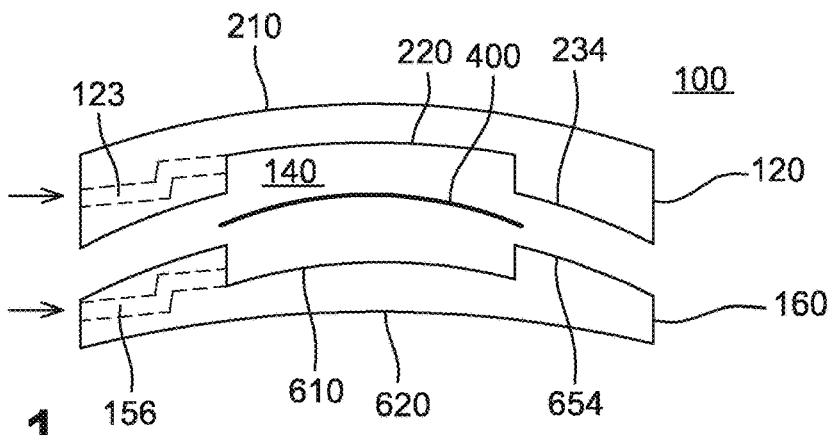
FIG. 1 represents an exploded view of an ophthalmic lens 100 according to an embodiment of the present invention.
Figure 2:
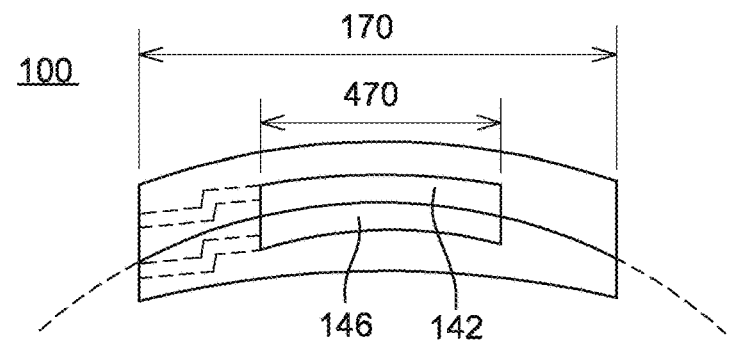
FIG. 2 shows a sectional view of an ophthalmic lens 100 with index matching according to the same embodiment of the present invention.

The core of the invention may be shown on FIG. 1: mechanically the glass 100 will be made from a half 120 and another half 160. These two halves may be each made in a different material: one half 120 will have a high index of refraction, the other half 160 will have a low index of refraction. In each half, the solid transparent constituting the half will have an index of refraction which may be matching the index of refraction of the fluid of the same half. Each half will thus be constituted from a solid material and a fluid, but optically this will be equivalent of having a single material, because of the index match. After assembly of the glasses and filling with the fluids an outside observer will not see any of the internal surfaces which may be separating the fluid from the solid. So the fluid's circuitry for instance will become invisible. Also the bottom part of the main chamber 140 will become invisible.

"Glass" does not exclusively mean "silicate glasses". Indeed, in the present invention, the term "glass" means a material or a composition that is transparent to visible light or visible spectrum, which is the portion of the electromagnetic spectrum visible to the human eye. Or it also means a piece part made from those materials.

Optically the lens 100 will be similar to a doublet by an association of first lens 120 and a second lens 160 with two different optical materials. The overall optical power, and more generally the overall optical characteristics like refraction and light scattering or dispersion, may be depending in a predictable way from the different characteristics of the geometry of the three important surfaces: the two external surfaces and the separation surface. As external surfaces, which may be a first primary surface 210 of first lens 120 and second secondary surface 620 of the second lens 160, this separation surface will be either a portion of sphere of given radius $R_{sep}$, or an aspherical surface which may be close to that shape.

Figure 3:
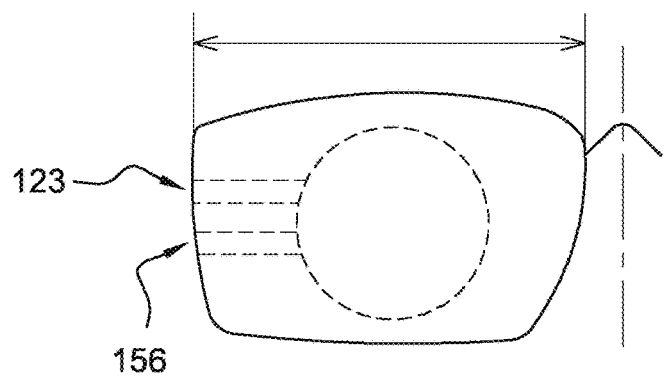
FIG. 3 illustrates a face view of an ophthalmic lens 100 according to the same or another embodiment of the present invention.

The principle of the variable lens may be that the membrane 400 may be stretched across all the central opening of the lens. This central opening, as shown on FIG. 3 may be circular. The membrane 400 edges may be fixed by the edges of this circular opening. This implies that the shape of the deformable membrane 400 may be always spherical, with a variable radius of curvature. At one given position of the deformable membrane 400, its radius of curvature will coincide with the radius of curvature $R_{sep}$ of the separation surface between the two halves. The choice of that particular position (corresponding to either focus near or focus far) may be left to the product design. At all other positions of the deformable membrane 400, the radius of curvature of the membrane 400 will be different from the radius of curvature of the separation surface. In these settings of the lens will appear like a bifocal lens: a lens where two zones have different optical power (and thus two different refractive corrections), the transition between the two zones being sharp and invisible. In addition, the width of the transition zone should be as small as possible, i.e. there should be no gradient between the two zones.

The optical variation of this kind of lens relies on the index difference between the two fluids which may be liquids. It may be advantageous to choose an index difference between the two fluids as high as possible. For instance one can choose for the low index part an index in the range of 1.33 to 1.43, where a lot of solid transparent materials exist as well as inert fluids. For the high index part, one will choose preferentially the index in the range of 1.55 to 1.70 where a lot of materials exist. The table below gives some examples, which may be not exhaustive:

TABLE 1

High index solids

| High index solids | Typical refractive index nD |
|---|---|
| PET | 1.57 |
| PC (polycarbonate) | 1.58 |
| PS (Polystyrene) | 1.59 |

TABLE 2

High index liquids

| High index liquids | Typical refractive index nD |
|---|---|
| Half phenylated silicon oil | 1.55 |
| Di-phenyl di methyl germane | 1.575 |
| benzothioazole | 1.64 |
| α-chloronaphtalene | 1.633 |

TABLE 3

Low index liquids

| Low index liquids | Typical refractive index nD |
|---|---|
| Fluorinert (fluorinated liquids) FC77 | 1.28 |
| water | 1.33 |
| Fluorinated silicon oil | 1.365 |
| Silicon oil | 1.40 |

TABLE 4

Low index solids

| Low index solids | Typical refractive index nD |
|---|---|
| FEP (fluorinated amorphous polymer) | 1.34 |
| PHFIP 2-FA (polymeric material for optical fiber cladding) | 1.36 |
| PDMS elastomer | 1.41 |
| PCTFE (Polychlorotetrafluoroethylene) | 1.435 |

Of course there may be many transparent solids and liquids with various refractive properties, which may be impossible to list here. The list above intends to show that the choice of fluids may be vast and by mixing fluids one can reach a very good index match between those and the chosen materials.

It may be advantageous that the fluids and solids indices of refraction match as closely as possible. Nevertheless, it may be possible to accept a slight difference between the two indices, of the order of a few hundredths at maximum. When using a system with a slight mismatch of index, it might be that the cavity and the channels become slightly visible or only visible in bright light or in conditions of special illumination. This mismatch would be acceptable for the user, as they would not affect the functionality of the product.

Most of the optical properties of the system will not depend on the membrane 400 index of refraction, nor on its thickness, as long it may be homogeneous. Only the light transmission will slightly depend upon the index of refraction of the membrane 400, as it will be maximum when the index of the membrane 400 may be intermediate between the low index and the high index. Nevertheless, practically with typical liquids indices, the loss of light by reflection at the membrane 400 interface will always be less than 1.5%, in a large range of membrane's 400 index. Typically the membrane 400 thickness will be from a fraction of one micrometer to hundredths of micrometers (100 nm to 100 μm).

Materials for the membrane 400 include: PDMS and all siloxane variants, elastomers of various chemical compositions (Butadiene based etc. . . . ). Fluorinated compounds, especially soluble in solvents (THV221 from 3M™, copolymers and terpolymers sold by Piezotech™), AF1600 kind of Teflon like materials which may be soluble in fluorinated solvents, products sold by Cytonix™ etc. . . . Novolac resins and similar resins based on reactive species: epoxies, polyurethanes, CR39 like resins, transparent polyesters.

It could be also advantageous to use materials that may be deposited in thin films at low temperatures, like Hexamethyldisiloxane also known as HMDSO based materials evaporated in a chamber and deposited by PECVD (Plasma deposition). Soluble polymers (reactive or nonreactive) deposited by spin coating can also be used, like PMMA (polymethylmethacrylate), PC (Polycarbonate), PS (polystyrene), and all resins that may be used in microtechnology works. UV polymerizable products may be also good candidate, acrylics, thiolene, epoxys and other chemistries.

The membrane 400 may have to have a combination of mechanical properties (Young Modulus, Poisson ratio, elastic deformation domain) as well as physico-chemical (low equilibrium adsorption of liquids should occur in the material) and transparency.

Index of refraction of the membrane 400 could be preferably in the range between the two sides indices, mostpreferably at the geometric mean of both indices, in order to minimize the overall reflectivity of the membrane 400 interface for visible light.

The bottom part of the main chamber, which could be a second primary surface 220 of first lens 120 and/or the first secondary surface 610 of the second lens 160, would be made optically invisible by the index matching. Nevertheless, in case of index slight mismatch, it may be advantageous to have a surface with good optical quality: its shape should be either spherical or close to spherical, in order not to create any distortion for the wearer.

For the same reason of possibility of a slight index mismatch, all surfaces of separation between the liquid and the solid should be polished surfaces with a very low roughness ($R_a$<100 nm RMS, precisely $R_a$<50 nm RMS and preferably $R_a$<20 nm RMS), in order to minimize residual light scattering at these interfaces. The RMS roughness may be measured via a profilometer.

Reversely all these design principles will allow to increase the index mismatch acceptable window.

Same principles apply for the channel shape and design than for the bottom cavity.

Figure 4:
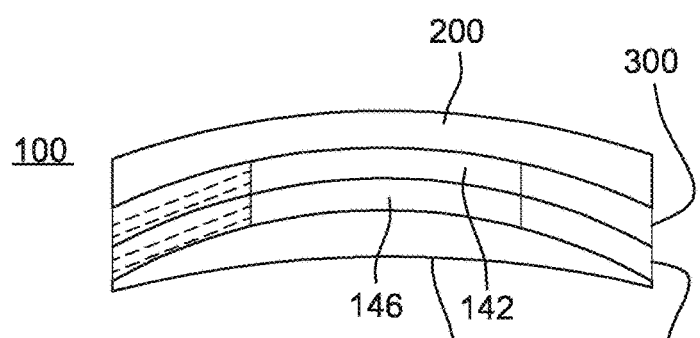
FIG. 4 presents a sectional view of an ophthalmic lens 100 with a first primary glass 200, a second primary glass 300, a first secondary glass 500 and a second secondary glass 600 according to another embodiment of the present invention.

In FIG. 4, it is shown an ophthalmic lens 100 where more separation surfaces may be used: this solution may use 2 to 4 different materials. The two materials which may be index matched to the primary fluid and the secondary fluid and either one of these materials for making the outer shells, or a third material like CR39 or PC (polycarbonate), which may be any polymer usable for ophthalmic lenses, as shown in FIG. 4. This last solution would be advantageous, as the outer surfaces would be similar to conventional glasses, with the possibility of benefiting from all surface treatments which have been developed over the years in the ophthalmic industry for spectacles like anti-reflection coatings, anti-scratch, anti-fog, color coatings and so on. It may be also possible to use 4 different materials for the different shells, or even more, according to any combination of preceding concepts.

Figure 5:
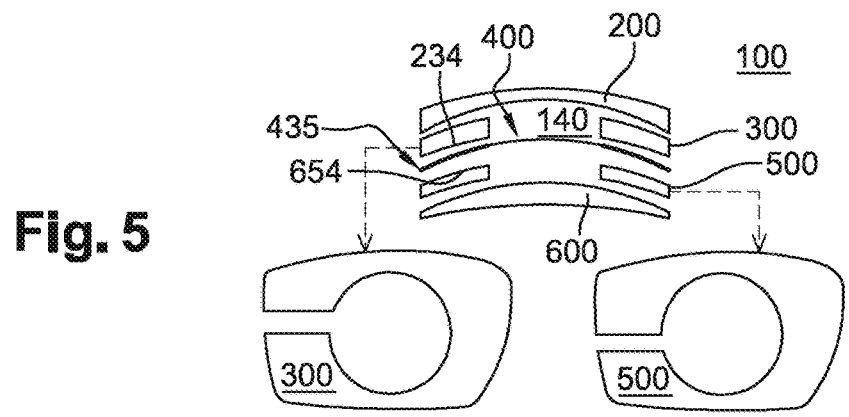
FIGS. 5 and 6 shows chamber cross-section with supporting membrane 400 and chambers sizes according to different embodiments of the present invention.

As it may be observed in FIG. 5 a variant where the channels may be more open than in the preceding sketches and the membrane 400 may be supported by supporting portion 435 which may be thicker and more rigid than the deformable membrane 400. Supporting portion 435 and deformable portion 470 could be made from the same material or not. The stack of FIG. 5 may use the variant just above, from top to bottom:

- the first primary glass 200, may be made from a conventional material, like CR39, supporting all sorts of coatings needed in a pair of spectacles;
- the second primary glass 300 may have a central opening and a channel to the outside. This part may be index matched with the primary fluid;
- the membrane 400, with a supporting portion 435 may have a circular central opening which may be covered with the thin deformable membrane;
- the first secondary glass 500 may have with the same central opening and a channel to the outside. This piece may be index matched to the second liquid;
- the second secondary glass 600 could be also made with the same material as the front shell.

Figure 6:
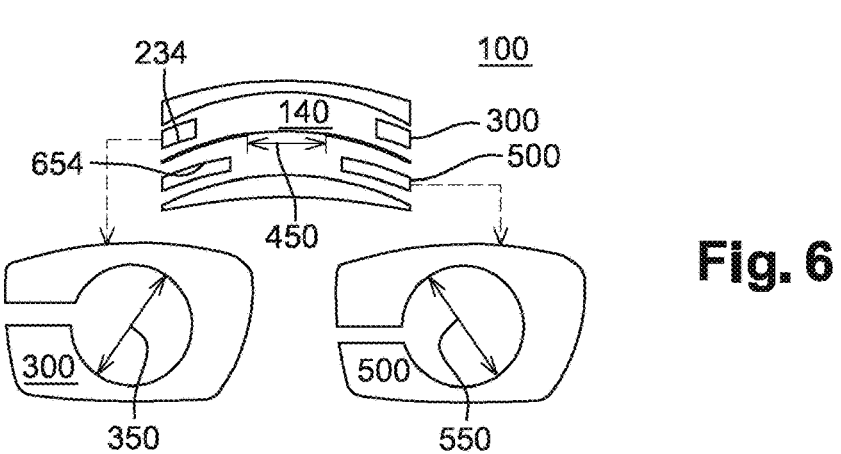

The FIG. 6 may show an asymmetric variant of FIG. 5: here the boundaries between the fluid and the solid may not have the same diameter, and possibly not the same shape, for both compartments.

All separating surfaces between these shells may have to be quite well defined. In particular the different radius of curvature of all separating surfaces and front and back surfaces will determine the overall optical power of the overall composite lens, which may be not variable like in a single focal lens. Presumably this may be adjusted to the refraction error of the user for the far vision. As for every other correction spectacles, it may be possible to engineer the different surfaces to include corrections for astigmatism, or prisms or any feature to correct for eye's aberrations. The only difference may be to have in the central zone an additional optical power for adjusting the vision to all distances, from far to reading. In the present application, the terms central zone or central portion may relate to the central zone or central portion of the membrane 400.

Practically one example of realization according to FIG. 5 would be to design the glass with all separating surfaces being spherical, except the rear surface i.e. the second secondary surface 620 of the second lens 160. This second secondary surface 620 could be a free-form surface, allowing including the prismatic and astigmatism corrections, as well as part of the refraction correction needed for myopia or hypermetropia, the other part being located at the front surface 210 and the intermediate surface.

Figure 7:
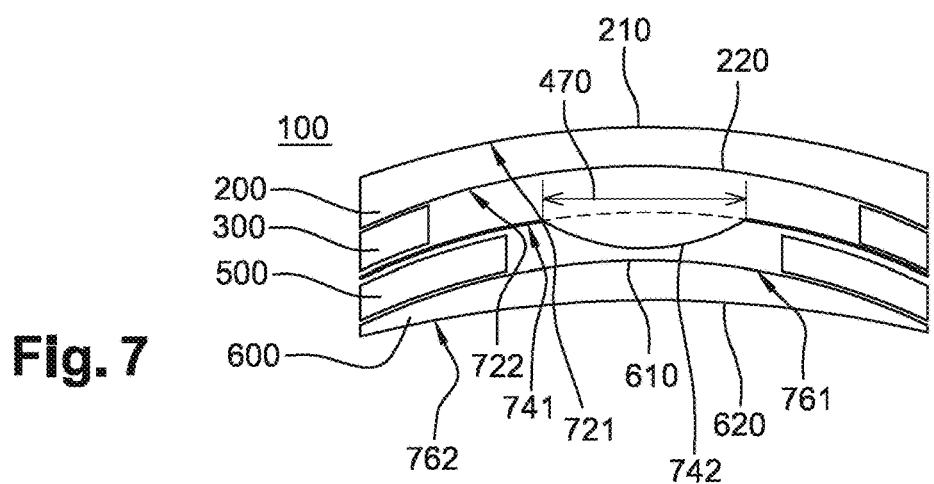
FIG. 7 illustrates how the membrane of the ophthalmic lens 100, according to another embodiment of the present invention, deforms when the variable zone is activated: dotted line corresponds to far vision, and solid line to the near vision.

The FIG. 7 summarizes the optical stack of the glasses with the membrane extremes positions: in the case where the primary glass has an index higher than the secondary glass, the dotted line will show the far vision set, while the continuous line shows the near vision position for the membrane. The rest position of the membrane is to be flat (not shown) in-between those two extreme positions.

Figure 8:
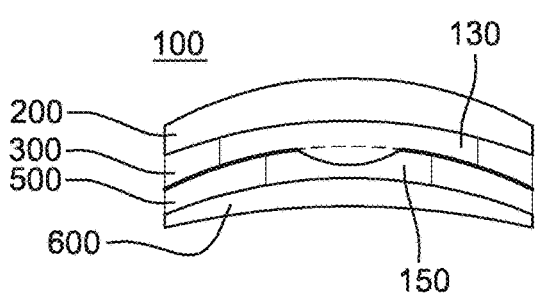
FIG. 8 shows a positive sphere correction at far vision for hyperopic patients according to another embodiment of the present invention; and, FIG. 9 presents a negative sphere correction at far vision for myopic patients according to another embodiment of the present invention.
Figure 9:
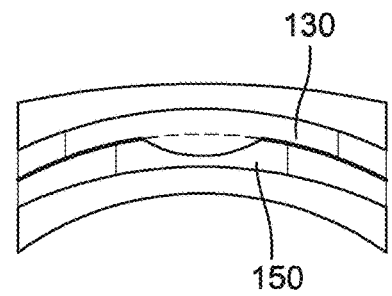

These FIGS. 8 and 9 show how the patient correction will be taken into account: in order to have a good refraction correction, each patient's eye should be measured for infinity vision: prismatic, astigmatism and sphere errors like myopic or hypermetropic for example. This correction will be included in the front and/or rear surfaces of the composite glass, as shown on the figure. The figure shows a particular case where both the rear and front surfaces may be curved to participate to the refraction error correction, but it may be possible to use only one surface. It is also possible, as in industry standards, to use the front surface for sphere correction and use the freeform manufacturing of rear surface for correcting astigmatism and more complex corrections. By front surfaces, respectively rear surfaces, we mean the air-primary glass interfaces and respectively air-secondary glass interface. It is also possible to use the separating surface to participate also to the patient's refractive corrections.

Detailed Description of the Invention According to a $1^{st}$ Embodiment

According to a first embodiment, the present invention relates to an ophthalmic lens 100 for spectacle as shown in FIG. 1. This ophthalmic lens 100 may comprise a primary glass 120, a secondary glass 160, a main chamber 140, a membrane 400, a primary fluid and a secondary fluid.

The primary glass 120 may comprise a first transparent material. This first transparent material may have a refractive index that may be chosen among one of the Table 1.

The primary glass 120, as shown in FIG. 1, may have the first primary surface 210 and the second primary surface 220. These surfaces may be configured to transmit light from one side or extremity to the other one. More precisely, the primary glass 120 may be configured to transmit light from the first primary surface 210 to the second primary surface 220 through the first transparent material.

The light may go further and may cross the main chamber 140 and the membrane 400 such as to reach the secondary glass 160.

The secondary glass 160 may comprise a second transparent material. This second transparent material may have a refractive index that may be chosen among one of the Table 4.

The secondary glass 160, as shown in FIG. 1, may have a first secondary surface 610 and the second secondary surface 620. These surfaces may be also configured to transmit light from one side or extremity to the other one. More precisely, the secondary glass 160 may be configured to transmit light from the first secondary surface 610 to the second secondary surface 620 through the second transparent material.

The main chamber 140 may have a main volume comprised between the second primary surface 220 and the first secondary surface 610 and the main chamber 140 may be defined between the second primary surface 220 and the first secondary surface 610.

In all embodiments, there may be a membrane 400, which may comprise a deformable portion 470, which may be located in the main chamber 140. Indeed, this deformable portion 470 may be partially comprised in the main chamber 140 and may separate totally or partially the main chamber 140 in at least a first chamber 142 and a second chamber 146. The first chamber 142 may be configured to comprise the primary fluid and it, namely the first chamber 142, may be comprised between the second primary surface 220 of the primary glass 120 and the deformable portion 470.

On other side of the membrane 400, there may be the second chamber 146. This chamber may be configured to comprise the secondary fluid and it, namely the second chamber 146, may be comprised between the deformable portion 470 and the first secondary surface 610.

In order to render invisible the interface between glass and fluid, the primary glass 120 may have a primary glass 120 refractive index and the primary fluid may have a primary fluid refractive index that may be actually near from each others. Concretely, the difference between the primary glass 120 refractive index and the primary fluid refractive index may be comprised between $0.1 \times 10^{-3}$ and $25 \times 10^{-3}$. This may be the same case for the interface between the secondary glass 160 and secondary fluid.

The secondary glass 160 may have a secondary glass refractive index and the secondary fluid may have a secondary fluid refractive index, and the difference between them, namely, the difference between the secondary glass refractive index and the secondary fluid refractive index may be comprised between $0.1 \times 10^{-3}$ and $25 \times 10^{-3}$.

It might be unnecessary to precise that the thickness of the membrane 400 may be so thin that the interface between the primary fluid and the membrane 400 and between the secondary fluid and the membrane 400 does not hinder the sight of the patient.

During manufacturing, the membrane 400 may be placed either on the primary glass 120 or on the secondary glass 160. More precisely, the primary glass 120 may comprise an intermediate primary surface 234 surrounding at least partially a primary opening wherein the membrane 400 may be placed. In this configuration, the membrane 400 may be placed in a position that may be described as rest position.

Similarly to the primary glass, the secondary glass may comprise an intermediate secondary surface surrounding at least partially a secondary opening. The intermediate primary surface and the intermediate secondary surface are configured to minimize residual light scattering at their interface and to correct the refraction errors of the patients at a given object distance Another way to fabricate the ophthalmic lens 100 might be to place the membrane 400 on an intermediate secondary surface 654 and more exactly to place the membrane 400 at the level of the secondary opening that may be called rest position since no pressure may be put on the membrane 400.

The first chamber 142 may comprise a first volume that may be sealed by the membrane 400 and the second chamber 146 may comprise a second volume, which may be also sealed by the membrane 400. In others words, the first volume and the second volume may be completely impermeable which means that no leak may permit fluid communication between the chambers.

The aforementioned chambers, namely the first chamber 142 and the second chamber 146, may be configured to increase or decrease their volume. Actually, this may be the membrane 400 which may be configured to increase or decrease the volume of the chambers. Indeed, the deformable portion 470 of the membrane 400 may be configured to be deformed between a first position and a second position. As already mentioned, the rest position may be located at the level of the primary or secondary opening when no pressure may be applied and the membrane 400 elastically deforms itself between the first position and the second position which may be located on both sides of the rest position. This technical feature may have the advantage that a portion of the resilient force of the membrane 400 may be used, when the membrane 400 come back to the rest position and no pressure may be applied. This may allow saving energy.

In order to avoid undue burden on the membrane 400, when the chambers may be filled with the primary fluid and the secondary fluid, the relative density may be matched so that the primary fluid having a first relative density and the secondary fluid having a second relative density. The ratio between the first relative density and the second relative density may be comprised between 0.9 and 1.2, in particular between 0.95 and 1.06 and preferably between 0.99 and 1.01. Thus, thanks to this configuration, the gravity force may have no influence on the fluid and indirectly on the membrane 400. In others words, no distortion appears on the membrane 400 since the hydrostatic pressures may be equivalent on both sides of the membrane 400.

The density match between the primary fluid and the secondary fluid may be combined to the mechanical properties of the membrane 400, in particular the lateral tension which is indirectly deduced from the deformation-pressure curve, and to the material properties of the membrane 400, in order to optimize the optical quality of the lens: when the ophthalmic lens 100 is operated vertically, which means that the optical axis is horizontal, there is a significant height difference between top and bottom of the ophthalmic lens 100, such that hydrostatic pressure can vary with height. When there is a perfect match of density of the primary fluid and the secondary fluid, on both sides of the membrane 400, this pressure can be equilibrated on both sides: even if the absolute value of the pressure varies, the pressure difference between one side and the other side of the deformable membrane 400 can be cancelled everywhere.

On other side, when there is a density mismatch, then this mismatch induces some deformations of the membrane 400, resulting in optical «coma» aberration. It has been found that there is a region of the parameter space where this optical aberration is below the specification, such that the optical quality is better. The following table 5 summarizes few configurations of the primary fluid and the secondary fluid and of the membrane thickness.

In table 5, the density mismatch ratio represents the ratio between the first relative density of the primary fluid and the second relative density of the secondary fluid. As it may be construed, an optical quality is achieved when the gradient of optical power between top and bottom of the ophthalmic lens 100 is less than 0.25 D. In others words, an optical quality is achieved when the ratio between the first relative density and the second relative density is comprised between 0.9 and 1.1 and when the membrane thickness is less than 10 μm, in particular when the ratio between the first relative density and the second relative density is comprised between 0.95 and 1.05 and when the membrane thickness is less than 5 μm and preferably when the ratio between the first relative density and the second relative density is comprised between 0.99 and 1.01 and when the membrane thickness is less than 1 μm.

TABLE 5

Density match criteria

| | INPUT | | | OUTPUT | |
| --- | --- | --- | --- | --- | --- |
| | | | | Maximum value of | |
| | | | | (Thickness × | Maximum thickness, | Maximum thickness, |
| | Diameter of the deformable membrane (mm) | Lateral Tension of the membrane (N/m) | Young modulus) of the membrane (μm*GPa) | assuming a 2 GPa Young modulus (μm) | assuming a 0.4 GPa Young modulus (μm) |
| Density mismatch | | | | | |
| 0.9–1.1 | 20 | 0.1 | 3.0 | 1.5 | 7.5 |
| | 20 | 1.0 | 2.0 | 1.0 | 5.0 |
| | 30 | 3.0 | 1.0 | 0.5 | 2.5 |
| 0.95–1.05 | 20 | 0.1 | 1.2 | 0.6 | 3.0 |
| | 20 | 1.0 | 0.8 | 0.4 | 2.0 |
| | 30 | 3.0 | 0.3 | 0.15 | 0.75 |

TABLE 5-continued

Density match criteria

| | INPUT | | OUTPUT | | |
|---|---|---|---|---|---|
| Density mismatch | Diameter of the deformable membrane (mm) | Lateral Tension of the membrane (N/m) | Maximum value of (Thickness × Young modulus) of the membrane (μm*GPa) | Maximum thickness, assuming a 2 GPa Young modulus (μm) | Maximum thickness, assuming a 0.4 GPa Young modulus (μm) |
| 0.99-1.01 | 20 | 0.1 | 0.2 | 0.1 | 0.5 |
| | 20 | 1.0 | <0.1 | <0.1 | <0.25 |
| | 30 | 3.0 | <0.1 | <0.1 | <0.25 |

The intermediate secondary surface 654, previously described, may be comprised by the secondary glass 160 and it, namely the Intermediate secondary surface 654, may surround at least partially the secondary opening. Here also, a particular attention should be paid at the interface between the intermediate primary surface 234 and the intermediate secondary surface 654 and in some other embodiment the same attention should be paid to the interface between the intermediate primary surface 234 and the membrane 400 and the intermediate secondary surface 654 and the membrane 400. Effectively, the interface may be configured to minimize residual light scattering. Otherwise, the patient may have an unpleasant sensation when the eye looks far and at the extremity of the sight field.

As it may be constructed from the reader, a particular attention may be paid to always offer an ophthalmic lens 100 as clear as possible and with an improved comfort.

Detailed Description of the Invention According to a 2$^{nd}$ Embodiment

In this second embodiment, the entire aforementioned technical feature may be more or less the same in this embodiment. However, in this second embodiment, the membrane 400 may comprise a supporting portion 435 partially comprised between the intermediate primary surface 234 and the intermediate secondary surface 654. This supporting portion 435 may surround the deformable portion 470 and in this configuration, the supporting portion 435 may offer the advantage to increase the size of the chambers and simultaneously to decrease the weight or the quantity needed for the primary and/or the secondary glass 160. The technical feature may lead to decrease the cost, increase the sight comfort and/or facilitate the manufacturing. Indeed, since the primary glass 120 and the secondary glass 160 may have different refractive index and made of different material, the first chamber 142 may have a first chamber shape and the second chamber may have a second chamber shape, which may have different shape and/or dimension from each others. In others words, the first chamber shape may be different of the second chamber shape.

Detailed Description of the Invention According to a 3$^{rd}$ Embodiment

In this third embodiment, the difference with the previously mentioned embodiments resides in the composition of the primary glass 120 and secondary glass 160. Indeed the primary glass 120 may comprise a first primary glass 200 and a second primary glass 300, and/or the secondary glass 160 may comprise a first secondary glass 500 and a second secondary glass 600.

The first primary glass 200 may have a first primary glass refractive index and the second primary glass 300 may have a second primary glass refractive index. The first primary glass refractive index may be selected among one refractive index present in the Table 1, or from any other optical material. It might be the same for the second primary glass refractive index.

The first secondary glass 500 may have a first secondary glass refractive index and the second secondary glass 600 may have a second secondary glass refractive index. The first secondary glass refractive index may be selected among one refractive index present in the Table 4. It might be the same for the second secondary glass refractive index.

The difference between at least one of the first primary glass refractive index and the second primary glass refractive index and the primary fluid refractive index may be comprised between $0.1 \times 10^{-3}$ and $25 \times 10^{-3}$ and the difference between at least one of the first secondary glass refractive index and the second secondary glass refractive index and the secondary fluid refractive index being comprised between $0.1 \times 10^{-3}$ and $25 \times 10^{-3}$. This technical feature may be particularly advantageous since the difference between the glasses and the fluids may be negligible the patient may have this feeling that the mechanism may be almost invisible which increases significantly the comfort of the patient.

This technical feature may be really convenient since the second primary glass 300 may comprise the primary channel configured to convey the primary fluid and to emerge into the first chamber 142 or the first secondary glass 500 may comprise a secondary channel configured to convey the secondary fluid and to emerge into the second chamber 146, the primary channel comprising the primary fluid and the secondary channel comprising the secondary fluid may be more or less invisible since the refractive index may be matched.

In this entire embodiment, the primary fluid may be conveyed in the first chamber 142 via a primary fluid passage 123 and the secondary fluid may be conveyed in the second chamber 146 via a secondary fluid passage 156.

The primary fluid passage 123 may comprise a primary channel configured to fluidly communicate with the first chamber 142. This primary channel may be, according to one of the aforementioned embodiment, partially delimited by the primary glass 120 and partially delimited by the membrane 400 or the secondary glass 160. For some manufacturing reasons, this technical feature might be interesting if the secondary glass 160 could not be bored.

The secondary fluid passage 156 may comprise a secondary channel configured to fluidly communicate with the second chamber 146. This secondary channel may be, according one of the aforementioned embodiment, partially delimited by the secondary glass 160 and partially delimited by the membrane 400 or the primary glass 120. For some manufacturing reasons, this technical feature might be interesting if the secondary glass 160 could not be bored.

In one embodiment, the primary fluid passage 123 and the secondary fluid passage 156 may be placed at different level in order to avoid to constraint the membrane 400 in the other fluid passage when one fluid may be conveyed in its chamber such as to facilitate external fluidic connection.

In another embodiment, the primary channel may be totally delimited by the primary glass 120. It may be the same for the secondary channel. Which means that secondary channel may be totally delimited by the secondary glass 160.

It is clear from the present description, that the primary channel or the secondary channel may have their own configuration independently from each other.

As it may be construed from the present description, in the entire embodiments the low refractive index part 160 may be comprised between the high refractive index part 120 and the eye. In practice, the primary glass refractive index may be greater than the secondary glass refractive index, and/or the first primary glass refractive index may be greater than the second secondary glass refractive index.

Some of these technical features might be found in a spectacle comprising such kind of ophthalmic lens 100 or in an eyepiece for a microscope, telescope, binocular microscope, magnifier, endoscope, optical viewfinder, donder zoom module, precision eyepieces, monoculars, binoculars, cameras and projectors, objective, or any apparatus used adapted to transform light before entering a human eye.

General public could benefit from these pairs in order to compensate for the loss of accommodation in everyday tasks (reading, watching TV, working on a computer, driving, making sport, etc. . . . ), but it could also be used by non-presbyopic people for increasing vision accuracy when performing highly precise tasks.

The invention claimed is:

1. An ophthalmic lens for a spectacle, comprising:
   a primary glass, the primary glass comprising a first transparent material; the primary glass having a first primary surface and a second primary surface, the primary glass being configured to transmit light from the first primary surface to the second primary surface through the first transparent material;
   a secondary glass, the secondary glass comprising a second transparent material; the secondary glass having a first secondary surface and a second secondary surface, the secondary glass being configured to transmit light from the first secondary surface to the second secondary surface through the second transparent material;
   a main chamber, the main chamber having a main volume located between the second primary surface and the first secondary surface; and
   a membrane, the membrane comprising a deformable portion, the deformable portion being partially located in the main chamber and totally separates the main chamber into at least a first chamber configured to comprise at least a primary fluid and a second chamber configured to comprise at least a secondary fluid, the first chamber being located between the second primary surface and the deformable portion, the second chamber being located between the deformable portion and the first secondary surface,
   wherein the primary fluid has a first relative density and the secondary fluid has a second relative density; the ratio between the first relative density and the second relative density being at least one of the following; between 0.95 and 1.06 and the membrane thickness being less than 5 μm, and between 0.99 and 1.01, and the membrane thickness being less than 1 μm.

2. The ophthalmic lens according to claim 1, wherein the primary glass having a primary glass refractive index and the primary fluid having a primary fluid refractive index are selected to have a difference between the primary glass refractive index and the primary fluid refractive index comprised between $0.1 \times 10^{-3}$ and $25 \times 10^{-3}$, and/or the secondary glass having a secondary glass refractive index and the secondary fluid having a secondary fluid refractive index are selected to have a difference between the secondary glass refractive index and the secondary fluid refractive index being comprised between $0.1 \times 10^{-3}$ and $25 \times 10^{-3}$.

3. The ophthalmic lens according to claim 2, wherein the primary glass comprises an intermediate primary surface surrounding at least partially a primary opening, the secondary glass comprises an intermediate secondary surface surrounding at least partially a secondary opening, the intermediate primary surface and the intermediate secondary surface are configured to minimize residual light scattering.

4. The ophthalmic lens according to claim 3, wherein the membrane is at least partially comprised between the intermediate primary surface and the intermediate secondary surface.

5. The ophthalmic lens according to claim 4, wherein the membrane comprises a supporting portion partially comprised between the intermediate primary surface and the intermediate secondary surface, and the supporting portion surrounds the deformable portion.

6. The ophthalmic lens according to claim 3, wherein the membrane comprises a supporting portion partially comprised between the intermediate primary surface and the intermediate secondary surface, and the supporting portion surrounds the deformable portion.

7. The ophthalmic lens according to claim 1, wherein the primary glass comprises an intermediate primary surface surrounding at least partially a primary opening, the secondary glass comprises an intermediate secondary surface surrounding at least partially a secondary opening, wherein the intermediate primary surface and the intermediate secondary surface are configured to minimize residual light scattering.

8. The ophthalmic lens according to claim 7, wherein the membrane is at least partially comprised between the intermediate primary surface and the intermediate secondary surface.

9. The ophthalmic lens according to claim 8, wherein the membrane comprises a supporting portion partially comprised between the intermediate primary surface and the intermediate secondary surface, and the supporting portion surrounds the deformable portion.

10. The ophthalmic lens according to claim 7, wherein the membrane comprises a supporting portion partially comprised between the intermediate primary surface and the intermediate secondary surface, and the supporting portion surrounds the deformable portion.

11. The ophthalmic lens according to claim 7, wherein the deformable portion is configured to be deformed between a first position, a second position and a rest position located at a level of the primary or secondary opening; the first position and the second position are configured to be located on both sides of the rest position.

12. The ophthalmic lens according to claim 1, further comprising a primary fluid passage comprising a primary channel configured to convey the primary fluid and to emerge into the first chamber; and a secondary fluid passage comprising a secondary channel configured to convey the secondary fluid and to emerge into the second chamber.

13. The ophthalmic lens according to claim 12, wherein the primary channel is partially delimited by the primary glass and partially delimited by the membrane or the secondary glass and/or the secondary channel is partially delimited by the secondary glass and partially delimited by the membrane or the primary glass.

14. The ophthalmic lens according claim 12, wherein the primary channel is totally delimited by the primary glass, and/or the secondary channel is totally delimited by the secondary glass.

15. The ophthalmic lens according to claim 1, wherein the first chamber has a first chamber shape and the second chamber has a second chamber shape, the first chamber shape is different of the second chamber shape.

16. The ophthalmic lens according to claim 1, wherein the primary glass comprises a first primary glass and a second primary glass, and/or the secondary glass comprises a first secondary glass and a second secondary glass; the first primary glass and the second primary glass have a first primary glass refractive index and a second primary glass refractive index respectively and the first secondary glass and the second secondary glass have a first secondary glass refractive index and a second secondary glass refractive index respectively; the difference between at least one of the first primary glass refractive index and the second primary glass refractive index and a primary fluid refractive index of the primary fluid is comprised between $0.1 \times 10^{-3}$ and $25 \times 10^{-3}$ and the difference between at least one of the first secondary glass refractive index and the second secondary glass refractive index and a secondary fluid refractive index of the secondary fluid being comprised between $0.1 \times 10^{-3}$ and $25 \times 10^{-3}$.

17. The ophthalmic lens according to claim 16, wherein the primary fluid refractive index is greater than the secondary fluid refractive index, and/or the first primary glass refractive index is greater than the second secondary glass refractive index.

18. The ophthalmic lens according to claim 16 wherein the second primary glass comprises a primary channel configured to convey the primary fluid and to emerge into the first chamber and/or the first secondary glass comprises a secondary channel configured to convey the secondary fluid and to emerge into the second chamber.

19. Spectacles comprising at least one ophthalmic lens according to claim 1.

* * * * *